(12) United States Patent
Sulur et al.

(10) Patent No.: US 12,616,655 B2
(45) Date of Patent: May 5, 2026

(54) TOPICAL ANTIBIOTIC CONTAINING PHARMACEUTICAL COMPOSITION FOR BACTERIAL INFECTIONS AND WOUND HEALING

(71) Applicant: Vishagan Vanangamudi Sulur, Chennai (IN)

(72) Inventors: Vishagan Vanangamudi Sulur, Chennai (IN); Vanangamudi Subramaniam Sulur, Chennai (IN); Madhavan Srinivasan, Chennai (IN)

(73) Assignee: Vishagan Vanangamudi Sulur, Chennai (IN)

( * ) Notice: Subject to any disclaimer, the term of this patent is extended or adjusted under 35 U.S.C. 154(b) by 803 days.

(21) Appl. No.: 17/635,644

(22) PCT Filed: Oct. 19, 2020

(86) PCT No.: PCT/IB2020/059815
§ 371 (c)(1),
(2) Date: Feb. 15, 2022

(87) PCT Pub. No.: WO2021/079254
PCT Pub. Date: Apr. 29, 2021

(65) Prior Publication Data
US 2023/0190647 A1 Jun. 22, 2023

(30) Foreign Application Priority Data

Oct. 24, 2019 (IN) .............................. 201941043186

(51) Int. Cl.
| | |
|---|---|
| *A61K 9/06* | (2006.01) |
| *A61K 9/00* | (2006.01) |
| *A61K 31/7048* | (2006.01) |
| *A61K 47/36* | (2006.01) |
| *A61K 47/42* | (2017.01) |
| *A61P 17/02* | (2006.01) |

(52) U.S. Cl.
CPC .............. *A61K 9/06* (2013.01); *A61K 9/0014* (2013.01); *A61K 31/7048* (2013.01); *A61K 47/36* (2013.01); *A61K 47/42* (2013.01); *A61P 17/02* (2018.01)

(58) Field of Classification Search
CPC .. A61K 9/0014; A61K 31/7048; A61K 47/36; A61K 47/42; A61K 9/06; A61K 31/351; A61K 9/107; A61P 17/02; A61P 31/04
See application file for complete search history.

(56) References Cited

U.S. PATENT DOCUMENTS

| | | | |
|---|---|---|---|
| 2005/0249691 A1* | 11/2005 | Monks | A61K 8/20 424/70.13 |
| 2012/0301508 A1 | 11/2012 | Hsieh et al. | |
| 2014/0213990 A1 | 7/2014 | Gorinshteyn | |
| 2014/0348911 A1* | 11/2014 | Ebensperger | A61P 17/02 128/200.14 |
| 2016/0367676 A1* | 12/2016 | Burnam | A61P 43/00 |

FOREIGN PATENT DOCUMENTS

| | | |
|---|---|---|
| CN | 202505827 U | 10/2012 |
| WO | 2010109417 A | 9/2010 |

OTHER PUBLICATIONS

International Search Report for PCT Application No. PCT/IB2020/059815, mailed Mar. 29, 2021.
Shenzhen Yuanxing Nano-Pharmaceutical Co Ltd, English Translation of "Hemostatic anti-inflammation antimicrobial applicator containing nano-silver" Chinese Patent No. CN202505827, granted Oct. 31, 2012.
Okur et al., "An alternative approach to wound healing field; new composite films from natural polymers for mupirocin dermal delivery" Saudi Pharm J. Jul. 2019;27(5):738-752. doi: 10.1016/j.jsps.2019.04.010. Epub Apr. 20, 2019. PMID: 31297030; PMCID: PMC6598503.

* cited by examiner

*Primary Examiner* — Snigdha Maewall
(74) *Attorney, Agent, or Firm* — Andrus Intellectual Property Law, LLP

(57) ABSTRACT
A Pharmaceutical composition for treating bacterial skin infections, burns and wounds is disclosed. It comprises an active ingredient, preferably Mupirocin, a biopolymer, preferably Chitosan, with molecular weight ranging from 250,000 Da to 600,000 Da, and a degree of deacetylation of not less than 80%, hydrolyzed Collagen, preferably of type I, with molecular weight ranging from 3 kDa to 6 kDa, and an ointment base comprising emulsifying agents, glycols and solubilizers. The invention has improved stability than the existing ointments, it heals skin and re-epithelializes faster than existing treatments thereby reducing hospitalisation period.

19 Claims, No Drawings

TOPICAL ANTIBIOTIC CONTAINING PHARMACEUTICAL COMPOSITION FOR BACTERIAL INFECTIONS AND WOUND HEALING

FIELD OF INVENTION

The present invention relates to a Pharmaceutical composition for bacterial infections and wound healing. In particular, the invention relates to a pharmaceutical composition comprising an topical antibiotic pharmaceutically active agent; a biopolymer; hydrolysed collagen of type I; and an ointment base.

BACKGROUND OF THE INVENTION

The skin is the body's first barrier against bacteria that cause infections. Bacterial skin infections can affect a small spot or may spread, affecting a large area. They can range from a treatable infection to a life threatening skin condition. Common skin infections include cellulitis, erysipelas, impetigo, folliculitis and furuncles and carbuncles. Cellulitis is an infection of the dermis and subcutaneous tissue that has poorly demarcated borders and is usually caused by *Streptococcus* or *Staphylococcus* spp. Erysipelas is a superficial form of cellulitis with sharply demarcated borders and is caused almost exclusively by *Streptococcus*. Impetigo is also caused by *Streptococcus* or *Staphylococcus* and can lead to lifting of the stratum corneum resulting in the commonly seen bullous effect. Folliculitis is an inflammation of the hair follicles. When the infection is bacterial rather than mechanical in nature, it is most commonly caused by *Staphylococcus*. If infection of the follicle is deeper and involves more follicles, it moves into the furuncle and carbuncle stages and usually requires incision and drainage. All of these infections are typically diagnosed by clinical presentation and treated empirically.

Wounds are heterogeneous and the wound healing process is of a multifactorial nature, influenced by many factors and compounds introduced externally. The definition of wound pharmacology is the study of agents and their actions in wound environment. Three classes of agents are used in wound healing treatment. They are drugs, biologics and special biologics such as those produced by biotechnology. These agents come under the group of pharmacological products. The group of non-pharmacological products consist products with no direct pharmacological effect on wound healing. These can be divided into interactive and passive materials.

Numerous treatments both topical and systemic are currently employed for the treatment of primary, secondary bacterial infections, caused by gram +ve and gram −ve organisms, and for burns and wound healing. Topical and systemic bacterial infection treatment composition typically employs an active ingredient in combination with a carrier component. The active ingredients typically comprise an antibiotic/antibacterial such as Mupirocin, Fusidic Acid, Sodium Fusidate, Benzyl Benzoate, Tetracyclines, Neomycin, Gentamycin, Framycetin, Sisomicin, Ciprofloxacin, Povidine-Iodine and the like.

Primary Infections:

Three forms of impetigo are recognized on the basis of clinical, bacteriologic, and histologic findings. The lesions of common or superficial impetigo may contain group A β-hemolytic streptococci, *S. aureus* or both, and controversy exists about which of these organisms is the primary pathogen. The lesions have a thick, adherent, recurrent, dirty yellow crust with an erythematous margin. This form of impetigo is the most common skin infection in children. Impetigo in infants is highly contagious and requires prompt treatment.

The lesions in bullous (staphylococcal) impetigo, which are always caused by *S aureus*, are superficial, thin-walled, and bullous. When a lesion ruptures, a thin, transparent, varnish like crust appears which can be distinguished from the stuck on crust of common impetigo. This distinctive appearance of bullous impetigo results from the local action of the epidermolytic toxin.

Ecthyma is a deeper form of impetigo. Lesions usually occur on the legs and other areas of the body that are generally covered, and they often occur as a complication of debility and infestation. The ulcers have a punched out appearance when the crust or purulent materials are removed. The lesions heal slowly and leave scars.

*Streptococcus pyogenes* is the most common agent of cellulitis, a diffuse inflammation of loose connective tissue, particularly subcutaneous tissue. No absolute distinction can be made between streptococcal cellulitis and erysipelas. Clinically, erysipelas is more superficial, with a sharp margin as opposed to undefined border of cellulitis.

Folliculitis can be divided into two major categories on the basis of histologic location: Superficial and deep. The most superficial form of skin infection is staphylococcal folliculitis manifested by minute erythematous follicular pustules without involvement of the surrounding skin. In deep folliculitis, infection extends deeply into the follicle and the resulting perifolliculitis causes a more marked inflammatory response than that seen in superficial folliculitis. In sycosis barbae (barber's itch), the primary lesion is a follicular pustule pierced by a hair. Bearded men may be more prone to this infection than shaven men.

A furuncle (boil) is a staphylococcal infection of a follicle with involvement of subcutaneous tissue. The preferred sites of furuncles are the hairy parts or areas that are exposed to friction and macerations. A carbuncle is a confluence of boils, a large indurated painful lesion with multiple draining sites.

Erysipeloid, a benign infection that occurs most often in fishermen and meat handlers is characterized by redness of the skin (usually on finger or the back of a hand) which persists for several days. The infection is caused by Erysipelothrix rhusiopathiae.

Pitted keratolysis is a superficial infection of the plantar surface, producing a punched out appearance. The areas most often infected are the heels the ball of the foot, the volarpads and the toes. Humidity and high temperature are frequent aggravating factors. Gram +Ve coryneform bacteria have been isolated from the lesions.

Erythrasma is a chronic, superficial infection of the pubis, toe web, groin axilla and inflammatory folds. *Corynebacterium minutissimum* is responsible for this.

Trichomycosis involves the hair in the axillary and pubic regions and is characterized by development of nodules of varying consistency and colour. Coryne forms bacteria are associated with trichomycosis.

Secondary Infections:

Intertrigo is most commonly seen in chubby infants or obese adults. In the skin fold, beat, moisture and rubbing produce erythema, maceration or even erosions.

Acute infections eczematoid dermatitis arises from a primary lesion such as boil or a draining ear or nose, which are sources of infections exudates.

Pseudofolliculitis of the beard, a common disorder, occurs most often in the beard area of people who shave.

Ulcers are deep skin infections due to injury or disease that invade the subcutaneous tissue and on healing leave scars. Ulcers can be divided into primary and secondary ulcers, but all become secondarily infected with bacteria.

Wound Healing

There am two types of cutaneous wounds. They are a) Full-Thickness Wounds b) Partial-Thickness Wounds a) Full-Thickness Wounds:

The epidermis and the full thickness of the dermis are lost. The defect is deeper than the adnexa (hair follicles, eccrine sweat ducts). These wounds heal by contraction (associated with myofibroblast development), granulation tissue formation (with fibroplasia and neovascularization), and re-epithelialization. Contraction causes a 40% decrease in the size of the wound. Epithelialization occurs from the wound edges.

b) Partial-Thickness Wounds:

The epidermis and some portion of the dermis with parts of the adnexa remain in the wound bed. Such wounds are produced by shave excisions, curettage and electro-desiccation, dermabrasion, chemical peels, and carbon dioxide ($CO_2$) laser surgery. These wounds heal quickly through re-epithelialization from the wound edges and adnexal structures in the base of the wound. Wound contraction is minimal when only the most superficial portion of the dermis has been lost.

Some of the more commonly used active compounds found in topical. Primary and secondary bacterial skin infections treatment formulations include topical Fusidic Acid, Sodium Fusidate, Mupirocin, Benzyl Benzoate, Tetracyclines, Ncomycin, Gentamycin, Ciprofloxacin, Povidine-Iodine and the like.

OBJECTIVE OF INVENTION

The therapies available for treating topical bacterial infection and burn wounds are not entirely satisfactory in terms of the time taken for removing the infection, restoring damaged skin, and hospitalisation period in the case of traumatised infections.

Further, it is known that antibacterials such as Mupirocin are unstable which reduces the shelf life of products made using Mupirocin.

One object of the invention is to provide a topical pharmaceutical antibacterial composition that reduces time for removal of infection, restoring damaged skin and hospitalisation period in the cases where hospitalisation is required.

Another object of the invention is to provide an antibacterial composition that has improved shelf life.

BRIEF SUMMARY OF THE INVENTION

The present invention is directed to a topical ointment composition for treating primary and secondary bacterial skin infections, burns and wound healing containing a. An active ingredient. Mupirocin, used in treating primary and secondary bacterial skin infections with Chitosan (as a bio-polymer) which is an unbranched binary polysaccharide consisting of the two units N-acetyl-D-glucosamine and D-glucosamine with narrowly defined molecular weight ranging from 250,000 Da to 600,000 Da. and a degree of deacetylation of not less than 80%, b. Hydrolyzed Collagen, preferably of type 1, which is a polypeptide with molecular weight ranging from 3 kDa to 6 kDa, and c. An ointment base comprising emulsifying agents, glycols and solubilizers.

The present invention is also directed to a process making the aforementioned ointment and also for treating primary, secondary skin infections caused by both sensitive gram +ve organisms such as *Staphylococcus* spp, *Streptococcus* spp and anaerobic gram −ve organisms such as *Haemophilus* spp, *Enterobacter* spp. *Neisseria* spp, *Branhamella* spp, *Pasteurella* spp, *Proteus* spp, *Citrobacter* spp, *Bordetella* spp. The present invention is also indicated in the healing treatment of wounds caused by burns & excision/incision cuts & bruises.

DETAILED DESCRIPTION OF THE INVENTION

Other than in the operating examples or where otherwise indicated all numbers expressing quantities of ingredients is understood as being modified in all instances by the term "about".

Topical Anti-Bacterial Agents

Topical Anti-bacterial agents are intended to target skin for bacterial infections caused by *Staphylococcus aureus, Staphylococcus epidermidis*, Methicillin Resistance Staphylococcus Aureus (MRSA) etc. Anti-bacterial agents act by inhibiting cell wall synthesis by combining with bacterial ribosomes and interfering with mRNA ribosome combination. In another hypothesis it is believed that anti-bacterial agents induce ribosomes to manufacture peptide chains with wrong amino acids, which ultimately destroy the bacterial cell.

Mupirocin

Mupirocin is an antibiotic with a narrow spectrum of activity, principally gram positive bacteria. Mupirocin is an antibiotic produced by submerged fermentation of *Pseudomonas fluorescens*. The drug is a pseudomonic acid and is structurally unrelated to other currently available anti-infective agents. Mupirocin (Pseudomonic acid A) is the major fermentation metabolite of *Pseudomonas fluorescens* exhibiting antimicrobial activity; minor fermentation metabolites structurally similar to mupirocin and possessing similar yet less potent antimicrobial activity have been identified as Pseudomonic acids B, C, and D. Mupirocin is commercially available as the base and as the calcium salt. Mupirocin occurs as a white to off-white powder and has solubilities of 1 mg/mL in water and 0.5 mg/mL in alcohol at 20° C. The drug has a pKa of 5 at 22° C. The molecular formula of Mupirocin is $C_{26}H_{44}O_9$, and the molecular weight is 500.629 g/mol. It is a white colour powder soluble in ethanol.

Pharmacology

Mupirocin is an antibiotic that is used topically (on the skin) for the treatment of impetigo, a bacterial disease of the skin caused by *Staphylococcus aureus*, Betahemolytic *Streptococcus* and *Streptococcus pyogenes*. It also is used intranasally (inside the nose) by patients and some people who work in healthcare centers to eliminate Methicillin-Resistant *Staphylococcus aureus* (MRSA) that have colonized the inside of the nose.

Mechanism of Action

Mupirocin has been shown to strongly inhibit protein and RNA synthesis in *Staphylococcus aureus* while DNA and cell wall formation were also negatively impacted a lesser degree. The inhibition of RNA synthesis was shown to be a protective mechanism in response to a lack of one amino acid, isoleucine.

Pharmacokinetics

Systemic absorption of Mupirocin through intact human skin is minimal. Any mupirocin reaching the systemic circulation is rapidly metabolized, predominantly to inactive monic acid, which is eliminated by renal excretion.

Indications

Mupirocin is indicated for the treatment of secondarily infected traumatic skin lesions (up to 10 cm in length or 100 cm2 in area) due to susceptible strains of *S. aureus* and *S. pyogenes*. Most of the topical products are formulated as either creams or ointments.

It is indicated for the topical treatment of primary and secondary bacterial skin infections as follows:

Primary skin infections: Impetigo, Folliculitis, Furunculosis and ecthyma.

Secondary skin infections: infected dermatosis e.g. infected eczema, infected traumatic lesions, e.g. abrasions, insect bites, minor wounds and minor burns.

Prophylactically it may be used to avoid bacterial contamination of small wounds, incisions and other clean lesions and to prevent infection of abrasions and small cuts and wounds.

Mupirocin acts by inhibiting the isoleucyl transfer RNA Synthetase in bacteria and there by bacterial protein synthesis is arrested. Due to this particular mode of action and its unique chemical structure Mupirocin does not show any cross resistance with other clinically available antibiotics. Mupirocin shows little risk of selection of resistant bacteria if used as prescribed. Mupirocin has bacteriostatic properties at minimum inhibitory concentrations and bactericidal properties at the higher concentrations reached when applied locally.

Chitosan

Chitosan is used in the present invention as a functional excipient, which enhances the wound healing at the local site of action. Chitosan is an un-branched binary polysaccharide consisting of the two units N-acetyl-D-glucosamine and D-glucosamine linked in β (1→4) manner. The product is obtained by partial deacetylation of Chitosan leading to a degree of deacetylation of not less than 70%. Chitosan is extracted from the shells of shrimp and crab, both of which should be from edible sources suitable for human use. It was found that chitosan extracted at lower degrees of deacetylation is not effective in providing synergetic effect.

Chitosan reduces itching, a perfect solution for affected skin. Itching is a phenomenon, which can significantly restrict daily life causes of itching include mosquito bites, allergic reactions, sunburn, neurodermatitis, psoriasis, atopic dermatitis, urticaria and dry skin. Most of these general inflammatory diseases areas are accompanied by redness, swelling & blisters. The elderly especially suffer from itching due to a tendency towards extreme dry skin.

Chitosan accelerates wound healing. The combination of improved wound healing and antimicrobial activity makes Chitosan particularly useful for biomedical applications such as wound dressings, periodontal treatment. Chitosan is available in varying molecular weights ranging from 5000 Da to 5,000,000 Da. However, we have carefully chosen by trials the molecular weight in the chain range 250,000 Da to 600,000 Da, which alone would ensure superior therapeutic effect on the indications of the formulated product. The degree of deacetylation of not less than 80% is also critical for Chitosan to have more free amines to react with the anionic mucus membrane for better adhesion &rapid effect of wound re-epithelialization. Since initially all wounds excrete with exudates they are prone to infection. And thus any topical application on a fresh wound area should have endotoxin level preferably less than 100 IU per g to ensure faster wound healing.

Collagen

Collagen comes from the Greek word "kólla", meaning "glue" and the French-gène, meaning "something that produces". In other words, collagen is a "glue-producing" protein.

Collagen is the most abundant protein in human bodies, especially type I collagen. It's found in muscles, hones, skin, blood vessels, digestive system and tendons.

Amino acids are the building blocks of collagen. Body can produce collagen after it breaks down dietary amino acids from protein-rich foods like chicken, dairy, and meat. Vitamin C is necessary for collagen synthesis. It helps to connect collagen-forming amino acids together.

Types of Collagen

The most abundant protein in the body, collagen makes up more than one-third of your total protein. It's rich in glycine, proline, and hydroxyproline—the amino acid % that help your body make new collagen.

There are more than two dozen known types of collagen. However, around 90% of body's collagen is type I, the 5 most common types being:

Collagen I: Because it's the most abundant, type I is in almost every tissue of your body: tendons, skin, bones, cartilage, connective tissue and teeth. Type I collagen fibrils are incredibly strong. They can resist a lot of pressure without breaking, and gram for gram, collagen I is stronger than steel.

Collagen II: Found mostly in cartilage.

Collagen III: Type III can be found alongside type I and in muscles, organs, arteries, and a type of special connective tissue called reticular fiber, which forms the liver, adipose tissue, bone marrow, spleen, and more.

Collagen IV: Forms the basal lamina, a layer of the extracellular matrix—the net that supports, cells—that sits underneath the epithelium. Basically, the basal lamina gives external support to your skin cells.

Collagen V: Collagen V can be found in the bone matrix, cornea, and in the connective tissue that exists between the cells of the muscles, liver, lungs, and placenta (also known as the interstitial matrix).

Collagen and Wound Management

In most wounds, complete replacement of harmed tissue to its unharmed state is impossible. The wound has to be healed using extra material to reconnect the tissue.

Collagen helps skin heal:

1. Within seconds of the injury, collagen activates coagulation in the wound to stop the bleeding.

2. As the blood vessels form fibrils, fibroblasts—collagen factories—lay down more collagen (aka the "glue") until the scar looks firmer.

3. During the second week following the wound, leukocytes gradually abandon the wound area and cells start cranking out type I collagen—the type that makes up your normal skin.

An ointment is a viscous semisolid preparation containing APIs, which are used topically on a variety of body surfaces. The vehicle of an ointment is known as ointment base. The choice of a base depends upon the clinical indication of the ointment, and the different types of ointment bases normally used are:

Hydrocarbon bases, e.g. hard paraffin, soft paraffin

Absorption bases. e.g. wool fat, bees wax

Both bases are oily and greasy in nature which leads to the undesired effects like difficulty in applying the ointment to and its eventual removal from the skin. In addition this also leads to staining of the clothes of a user.

Human skin's pH value is between 4.5 and 6. A newborn baby's skin pH is closer to neutral (pH 7), but the skin quickly turns acidic. Nature has designed this probably to protect young children's skin, since acidity kills bacteria. As people become older, the skin becomes more and more neutral, and won't kill as many bacteria as before. This is why the skin gets weak and starts having problems. The pH value goes beyond 6 when a person actually has a skin problem or skin disease. This shows that it is necessary to choose topical that have a pH value close to that of skin of a young adult.

A slight shift towards the alkaline pH would provide a better environment for microorganisms to thrive. Active compounds in ointment formulations are available in ionized state, whereas in case of ointments these are present in non-ionized state. Generally, the cream/ointment formulations are the first choice of the formulators in design and development of topical dosage forms, as the cream/ointment formulations are cosmetically elegant, and also as the active compound is available in ionized state, and the drug can penetrate the skin layer fast which makes the formulation totally patient friendly. The pH of Mupirocin Ointment of the present invention is skin friendly and ranges between 6.8 and 7.2. On the other hand, ointments that are commercially available in the market have a pH above 7.5 and are greasy and staining. The higher pH of the commercially available products are irritant to the skin due to their alkalinity, whereas the current invention has a near neutral pH ensuring non-irritancy and which has been established through pre-clinical animal model evaluation.

Rationale for the Use of Antibacterial-Mupirocin with Chitosan and Hydrolyzed Collagen Combination in an Ointment Base:

In current dermatological therapy there are some unmet medical needs, which have to be addressed. For example, dermatological conditions are often caused by allergy accompanied by inflammation, irritation and itching and hence these conditions get further complicated by bacterial infections. Numerous topical treatments are currently employed in primary and secondary bacterial skin infections. However there is no effective therapy for protecting the skin, controlling superficial bleeding, wounds and burns. To meet this need also at affordable cost the current invention ensures a safe therapy to the dispersed segment of population across all countries/communities. The current invention—a novel ointment formulation—which is a unique combination of Chitosan, a biopolymer and Hydrolyzed Collagen of type I that have wound healing properties to build the skin matrix back to natural state along with the anti-bacterial Mupirocin for bacterial control/treatment of infections particularly those caused by *Staphylococcus aureus*.

Topical antibiotics like Mupirocin help prevent infections caused by bacteria that get into minor cuts, scrapes and burns. Treating minor wounds with Antibiotics like Mupirocin ensures healing. If the wounds are left untreated, the bacteria will multiply, causing pain, redness, swelling, itching, and oozing. Untreated infections can eventually spread and become much more serious.

The inclusion of Chitosan in the formulation has multitude attributes, which are very essential in treating skin ailments. The combination of Chitosan and Hydrolyzed Collagen of type I along with the antibacterial agent Mupirocin is unique and novel and is not available across the globe. The concept of the combination is justified by considering the physical, chemical and therapeutic properties of chitosan and collagen with the antibacterial agent Mupirocin. The applicant has found that the therapeutic effect of Mupirocin enhances by incorporation of chitosan and collagen.

Chitosan has properties of film forming and is biocompatible and non-allergenic ensuring skin re-epithelialization and helps in rejuvenating and regenerating the skin back to its normal state. In addition it also accelerates wound healing and provides the wound a barrier through a bio-degradable micro-film formation. It further controls the superficial bleeding caused by scratching ensuring through its cationic charge the mobility of pathogens. This alone provides a rapid wound healing effect.

The role of Collagen in the formulation is to build the matrix for rapid skin re-epithelialization and bring the skin back to its native state. In any anti-bacterial therapy, the antibacterial agents like Mupirocin address the control/treatment of infections. But issues like wound healing, skin regeneration and rejuvenation, bio-film protection of the skin, bleeding and mobility of pathogens from one site to another, etc. have not been addressed in prior-art thus far.

The current invention fills this gap by an innovative technology of incorporation of Chitosan and Collagen into the ointment matrix of Mupirocin thus establishing the essential requirements of accelerated wound healing addressing the gaps in the current therapy defined above.

Chitosan/Polyglucosamine is structurally similar to hyaluronan and is expected to assist scarless wound healing. Heparin enhances mitogen by induction and stabilization of fibroblast growth stimulating factor (FGF). Polyglucosamine may promote tissue growth and wound healing by forming complexes with heparin and acting to prolong the half-life of the growth factors. Chitosan's properties allow it to rapidly clot blood, and it has recently gained approval in the USA for use in bandages and other hemostatic agents. Burns/Cuts/Wounds can happen at any place and time and in the absence of immediate medical support—unattended wounds/cuts/burns often leads to complications and high likelihood of secondary bacterial/fungal infections and multiply manifold the originating medical condition needing a therapeutic response. The present invention would provide first line of response in terms of medical intervention, convenience, affordability, reliability, efficacy, safety which have a critical impact on the skin condition.

Currently no treatment is available to heal the wound and also to stop bleeding. During dermatological conditions, currently available therapies do not address the issues like protecting the skin, arresting the bleeding etc. The unique innovative formulation of the present invention takes care of the skin conditions by treating them along with protecting the skin and controlling the bleeding at the site. Thus this unmet gap is filled by this innovative technology and will be invaluable in minimizing/eliminating the problems in such cases. Further with ever increasing pressures on medical support systems and the attendant scarcity/high cost of the same, there is an emergent need all across the globe to address the following issues in such cases—

Patients waiting too long for treatment
Unwanted hospital stay
Avoidable frequency of visits to hospital
Reducing the length of stay is a key problem to be tackled in most cases.

The novel ointment of the present invention is most stable/efficacious at ambient conditions and does not need specific temperature control during transportation/storage thus achieving the social objectives to the benefit of the society at large. It has proven synergy and enhanced medicinal efficacy over mupirocin compositions that do not include either chitosan or collagen.

Furthermore, as described under prior art in patent number U.S. Pat. No. 6,489,358, Mupirocin has stability issues when it is not solubilized in compatible solvent. The current formulation has overcome this issue of stability by using proportions of solvents and co-solvents in optimized ratio to render a stable, safe and therapeutically enhanced formulation. If the active Mupirocin is not dispersed in the formulation through proper solvents it tends to rapidly degrade even when stored at mom temperature. Only with the right choice of solvents and more importantly with the incorporation of the biopolymer Chitosan and the natural peptide Collagen has the formulation of the invention been stabilized. The rate of degradation of the Active Mupirocin is found to be comparatively lower.

Advantages Achieved in the Present Invention are as Listed Below:— a) Through the novel approach adopted for the current invention, it has Mupirocin incorporated with Chitosan and Collagen for the first time as a stable ointment formulation.

b) The present formulation is indicated in the treatment of minor cuts, burns, excision and incision wounds and importantly for bacterial skin infections caused by gram +ve microorganisms.

c) The current composition of this formulation discloses an ointment which produces better therapeutic effect as compared with the presently available Mupirocin compositions such as T-Bact of GlaxoSmithKline (GSK) with good spread-ability and skin adherence ensuring enhanced penetration and diffusion of Mupirocin. In general currently available ointment compositions are greasy formulations and stick on the skin for long periods to ensure penetration, since they lack spread-ability. Whereas the formulation of the invention has addressed the greasiness issue and formulated a non-greasy ointment base with better spreadability for improving considerably penetration and diffusibility of the API.

The presence of the biopolymer and collagen in the composition produces better and longer skin adherence localizing the active to achieve enhanced activity in comparison to currently available market products.

According to one embodiment of this present invention, there is provided a composition for this topical treatment of bacterial skin infections/burns and wound healing on human skin. The composition contains:

a) From about 0.1% to about 5% by weight, preferably about 2% by weight, of an acid form active compound Mupirocin.

b) From about 0.01% to about 0.5% by weight, preferably about 0.05% by weight of Chitosan. The molecular weight chain length preferred for this current invention ranges from 250.000 Da to 600.000 Da.

TABLE 1

SPECIFCIATION OF CHITOSAN
ON SELECTED PARAMETERS

| PARAMETERS | GENERAL SPECIFICATION | SPECIFICATION FOR THE PRODUCT OF INVENTION |
|---|---|---|
| AVG MOLECULAR WEIGHT | <1000000 Da (as per USP/NF) | <600000 Da |
| DEGREE OF DEACETYLATION | 70%-95% (as per USP/NF) | >80% |
| BACTERIAL ENDOTOXIN | 300 IU/g | 100 IU/g | c) From about 0.01% to about 0.5% by weight, preferably about 0.05% by weight of Hydrolyzed Collagen of molecular weight ranging from 3 kDa to 6 kDa.

According to another embodiment of the present invention, there is also provided a process for treating primary, secondary bacterial skin infections and burns, wound healing involving contacting human skin with the above disclosed composition.

The invention therefore discloses a composition comprising:

a) An acid form active ingredient for treating primary, secondary bacterial skin infections and minor cuts, burns.

b) A Chitosan component, which is an unbranched binary polysaccharide consisting of two units N-acetyl-D-glucosamine and D-glucosamine, of specified molecular weight range c) A Collagen component, which is a peptide derived from marine source, of specified molecular weight range d) Anointment base.

In an embodiment of the invention, the acid form active ingredient is preferably Mupirocin.

In another embodiment, the acid form active ingredient, preferably Mupirocin, is present in the composition in an amount of from about 0.1% to about 5% by weight based on the weight of the composition.

In a further embodiment, Chitosan in present in the composition is present in an amount of from about 0.01 to about 0.5% by weight, based on the weight of the composition.

In a still further embodiment, the Hydrolyzed Collagen in present in the composition is of type I and present in an amount of from about 0.01 to about 0.5% by weight, based on the weight of the composition.

According to the preferred embodiment of the present invention, there is provided a composition for the topical treatment of bacterial skin infections, burns and wound healing on human skin, the composition comprising—from about 0.001% (w/w) to about 5% (w/w) by weight, prefer-
ably about 2% (w/w) of Mupirocin, from about 0.01% to
about 1% by weight, preferably about 0.05% by weight of
Chitosan. (Molecular Weight—300.000 Da to 600,000 Da)
and from about 0.01% to about 1% by weight, preferably
about 0.05% by weight of Hydrolyzed Collagen.

anointment base containing waxy materials, co-solvents,
acids, and buffering agents preservatives, anti-oxidants,
chelating agents, humectants, water, all weights based
on the weight of the composition, wherein waxy materials are selected from a group comprising
Polyethylene Glycols (PEG) such as PEG 400, PEG
500, PEG 1000, PEG 1200, PEG 1500, PEG 1800. PEG
2000, PEG 2200, PEG 3550 and PEG 4000 alone or in
combination and the like from about 5% (w/w) to 80%
(w/w), co-solvents are selected from a group comprising Propyl-
ene Glycol, Hexylene Glycol, PEG-200, 300, 400, 500
and the like from about 5% (w/w) to 80% (w/w), acids such as HCl, $H_2SO_4$, $HNO_3$, Lactic acid and the like
from about 0.005% (w/w) to 1% (w/w), thickeners such as Acrylamide/Sodium Acryloyldimethyl
Taurate Copolymer/isohexadecane and Polysorbate 80
(Brand Name—Sepineo P 600), Microcrystalline Cel-
lulose. Carboxymethyl Cellulose, Hydroxypropyl
Methyl Cellulose, Ethyl Cellulose and the like alone or
in combination from about 0.05% (w/w) to 10% (w/w).

preservatives are selected from a group comprising Meth-
ylparaben, Propylparaben, Chlorocresol. Potassium
sorbate. Benzyl Alcohol, Phenoxyethanol and the like
from about 0.05% (w/w) to 2.0% (w/w), anti oxidants are selected from a group comprising Buty-
lated Hydroxy Anisole, Butylated Hydroxy Toluene
and the like from about 0.05% (w/w) to 5% (w/w), chelating agents are selected from a group comprising
Disodium EDTA and the like from about 0.05% (w/w)
to 1% (w/w), The present invention will be further elucidated with
reference to the accompanying example, which is however
not intended to limit the invention in any way whatever.

A process has been achieved to ensure the addition of
Chitosan & Collagen along with the active drug molecule
Mupirocin for better shelf-life stability and enhanced thera-
peutic effect of the product.

TABLE 2

Composition of Mupirocin 2% w/w with Chitosan 0.05% w/w
and Hydrolyzed Collagen 0.05% w/w Ointment Formulation

| S. No. | Ingredients | Percentage of ingredients in the composition |
|---|---|---|
| 1 | Mupirocin | 2 |
| 2 | Benzyl Alcohol | 1 |
| 3 | Chitosan (Chitopharm-M) | 0.05 |
| 4 | Hydrolyzed Collagen | 0.05 |
| 5 | Disodium Edetate (EDTA Disodium) | 0.01 |
| 6 | Lactic Acid | 0.025 |
| 7 | Polyethylene Glycol-4000 | 18.0 |
| 9 | Phenoxyethanol | 0.5 |
| 10 | Acrylamide/Sodium AcryloyldimethylTaurate Copolymer/Isohexadecane&Polysorbate 80 | 2 |
| 11 | Hexylene Glycol | 5 |

12

TABLE 2-continued

Composition of Mupirocin 2% w/w with Chitosan 0.05% w/w
and Hydrolyzed Collagen 0.05% w/w Ointment Formulation

| S. No. | Ingredients | Percentage of ingredients in the composition |
|---|---|---|
| 12 | Purified Water | 2 |
| 13 | Polyethylene Glycol-400 | q.s. |

The therapeutic efficacy of topically applied innovative
antibacterial Mupirocin ointment with Chitosan and Colla-
gen is due to the pronounced antibacterial activity of the
active Mupirocin against the organisms responsible for skin
infections, the unique ability of active to penetrate intact
skin and also due to wound healing & soothing properties of
Chitosan and Collagen. The near neutral pH of the final
formulation has ensured non-irritation of the skin by its
friendly composition.

Wound Healing and Synergy

The formulation of the current invention has combinato-
rial effect of an anti-bacterial agent with the other ingredient
biopolymer Chitosan providing a micro-film over the
infected area preventing secondary infection. Chitosan also
reduces the blood clotting time in the affected area thus
preventing blood loss. Collagen aids in the epidermal stra-
tum ensuring re-epithelialization/rejuvenation of skin to its
original state after the bacterial treatment with the active
Mupirocin is achieved.

Experimental Data to Support Enhanced Efficacy, Synergy,
and Stability:

A number of studies were commissioned by Apex Labo-
ratories Private Limited on behalf of the applicant. These
are:

A. Efficacy determination of a ointment formulation of
mupirocin ointment of the invention in comparison
with mupirocin ointment of T-Bact ointment, of
GlaxoSmithKline (GSK) based on infected wound in
wistar rats, carried out in February, 2020, carried out by
Mahatma Gandhi Medical College & Research Insti-
tute. Sri Balaji Vidyapeeth Deemed University, Pillai-
yarkuppam, Cuddalore road, Puducherry-607403,
India.

The purpose of this study was to assess and compare the
efficacy of Mupirocin Ointment of the invention with Mupi-
rocin Ointment (T-Bact Ointment) of GSK in rat infection
model, which was expected to accurately reproduce the
pathophysiology of infected wound healing and serve as a
valid basis for further research on humans. The product of
the invention used for the tests included Mupirocin IP 2.0%
w/w in an Ointment base containing Biopolymer (Poly-β-
(1,4)-2-amino-2-deoxy-D-glucose) q.s., with Benzyl Alco-
hol IP 1.0% w/w and Phenoxyethanol IP 0.5% w/w used as
preservatives. A total of 24 animals were subjected to tests
grouped as follows:

Group I: Normal Control rats—With wounds—Without
Infection

Group II: Negative Control rats—With Wounds—With
MRSA infection

Group III: Rats treated with Standard Comparator (Mupi-
rocin Ointment—T-Bact Ointment from GSK)

13

Group IV: Rats treated with Test (Mupirocin Ointment of the invention) Wounds were created using punch biopsy method, as mentioned above and infected with MRSA, until the counts reached 7.03±0.37 log 10. Animals were assigned as per the following groups and treatments were carried out every day for a period of 12 days.

The following microbiological inference was drawn:

Group 2: There was continuous bacterial multiplication in this group as the wound was left untreated. After the study period the animals were treated with the conventional treatment Group 3: There was a reduction in the colony-forming units (CFUs) that were recovered from the wound of the animals in this group during the study period. This suggested that the animals were responding to the antibacterial ointment (T-Bact Ointment of GSK).

Group 4: A reduction in the number of CFUs was observed in all the animals of this group during the study period, suggesting a positive response to the antibacterial Mupirocin ointment of apex. This group showed a considerable reduction in the bacterial count (CFU) on day 6 and 9.

Statistical analysis of the microbiological, on the data for the two groups (Mupirocin Ointment of the invention and of T-Bact of GSK) led to the conclusion that, quantitatively, there were an earlier reduction in the number of CFUs of MRSA on day 6 and 9 in the group treated with Mupirocin Ointment of the invention.

The following histopathology inference was drawn: Histopathological examination report revealed a healthy tissue healing process in group 4 comparable with the normal and GSK's T-Bact Ointment-treated group and more tissue granulation tissue formation was seen in group 4. Also, histopathologically, more granulation tissue (healing tissue) was seen in group 4 compared to the other groups which goes in hand with the better wound contracture % (wound healing rate).

Finally, a hematological assessment was also carried out which revealed a non-infectious sample outcome for group 4 at the end of the study comparable with the Normal Control group. A healthy healing profile of the tissue inflammatory infiltrates is visible with the estimation of the blood parameters.

From the above study results obtained, it may be concluded that Mupirocin Ointment of the invention provides more effective and better wound healing outcome when compared to Mupirocin Ointment (T-Bact Ointment) of GSK. In other words, it is evident that the efficacy of the mupirocin was enhanced due to the presence of chitosan and collagen of carefully selected properties, thereby establishing a synergetic effect between mupirocin, chitosan and collagen.

Two other sets of experiments were carries out. These are:
Assessment of Efficacy of Mupirocin ointment and T-Bact Ointment on experimentally induced burn wound healing in Wistar rats; and
Assessment of Efficacy of Mupirocin ointment and T-Bact Ointment on experimentally induced excision wound healing in Wistar rats Both studies were carried out by RAK College Of Medical Sciences, Ras Al Khaimah, UAE, in December, 2019.

14

Summary of the outcome of these experiments are presented in terms of the period of epithelialization of Mupirocin Ointment against the reference product (T-Bact) in the table that follows.

TABLE 3

| | | Period Of Epithelialisation after Excision and Burn Wound Treatment: | | |
| Description | Control (Days) | Reference Product (T-Bact Ointment of GSK) (Days) | Mupirocin Ointment of Current Invention (Days) | Remarks |
| --- | --- | --- | --- | --- |
| Excision Wound | 19.12 ± 0.95 | 17.57 ± 0.92 | 16 ± 1.15 | |
| Burn Wound | 22.15 ± 0.25 | 21.50 ± 0.73 | 19.25 ± 1.19 | |

The pre-clinical efficacy study conducted in animal models for excision wounds, burn wounds and infected wounds reveal the rate of healing of the current invention product to be superior in comparison to the reference product tested.

The rate of epithelialization reveals faster healing for Mupirocin Ointment of Current Invention as observed in the above table, the healing with Mupirocin Ointment treated group has healed faster than the Control product and also T-back of GSK. The burn wound contraction on Day 16 was significantly higher at 79% for current invention and only 67% for T-back of GSK, whereas the control non-treated group produced only 40% of wound contraction.

A separate infected wound model study was conducted and the results conclude that at Day 12 the wound contraction measurement observed for Mupirocin Ointment was 75.2% and for the reference product was 69% only.

The significance in reduction in rate of hum wound healing is attributed to the presence of Chitosan and Collagen in the current invention. Chitosan and Collagen in combination with the active Mupirocin has resulted in the synergistic effect of wound healing which is not pronounced in the reference product having neither Chitosan or Collagen.

Moreover the bacterial culture study with the infected wound model showed no significant microbial colony formation at the wound site at the end of study in comparison to the reference product. This indicates that the presence of both Chitosan and Collagen has not hindered the antibacterial inherent property of the active Mupirocin in the current invention product.

The additional histopathological and hematological assessment reveal that the product of current invention has produced more granulation tissues during healing thus facilitating wound contraction. The hematological parameters assessed have indicated that the parameters are comparable to the normal skin. The above observations without any ambiguity portrait superior efficacy of our current invention.

The activity of Mupirocin along with Chitosan and Collagen produces synergistic effect on the affected skin assuring a considerable reduction in the treatment period. Chitosan and Collagen in the composition facilitates for the skin to set into its natural form. The synergism as found in the current composition is not found in any of the currently available market products. These claims were established through the results obtained from the animal model study conducted on rats for healing of burn wounds, excision wounds and infected wound models.

Stability of the Formulation:

Comparative Stability Data

Product Claim: Mupirocin 2% w/w (20 mg in 1 g)

Condition - 25° C./60% RH (Real-time stability guideline as per ICH - Q1A(R2))

| | | Assay Content (expressed as %) | | | | | Remarks % reduction in content |
| --- | --- | --- | --- | --- | --- | --- | --- |
| | Initial | $1^{st}$ Mth | $3^{rd}$ Mth | $6^{th}$ Mth | $12^{th}$ Mth | $15^{th}$ Mth | from initial assay |
| Marketed Product | 107.40% | 105.47% | 103.26% | 100.47% | 98.45% | 95.24% | 12.16% |
| Current Invention | 106.75% | 105.07% | 104.51% | 104.39% | 104.05% | 101.2% | 5.55% |

*The market product shelf-life indicated in the product pack was 12 months, however stability studies were continued for 15 months for comparative analysis.

The stability study reveals that the product of current invention when studied by stability guideline of ICH is more stable than the marketed product tested. The marketed product has shown decline of content to about 12% and whereas the current invention product showed only 5.6% reduction in the active content Mupirocin which decline is only half of the market product. The API Mupirocin being the same confirming to the same specification the current formulation has stabilized the molecule relatively far better than the innovator market product. This ensures that the therapy with the API molecule provide superior treatment in comparison with the market product."

It is evident from the above data that the stability of the product of invention is superior to that of the marketed product.

While the above description contains much specificity, these should not be construed as limitation in the scope of the invention, but rather as an exemplification of the preferred embodiments thereof. It must be realized that modifications and variations are possible based on the disclosure given above without departing from the spirit and scope of the invention. Accordingly, the scope of the invention should be determined not by the embodiments illustrated, but by the appended claims and their legal equivalents.

The invention claimed is:

1. A pharmaceutical composition for bacterial infections and wound healing, characterised in that said pharmaceutical composition comprises following components:

a topical antibiotic pharmaceutically active agent;

a biopolymer;

hydrolysed collagen of type I; and an ointment base;

wherein all components are mixed homogeneously to form an ointment of pH value between 6.8 and 7.2;

wherein said topical antibiotic pharmaceutically active agent is Mupirocin present in an amount between 0.1% (w/w) to 5% (w/w);

wherein said biopolymer is Chitosan present in an amount between 0.01% (w/w) to 0.5% (w/w); and wherein said hydrolyzed collagen of type I is present in an amount of from about 0.01 (w/w) and 0.5% (w/w).

2. The pharmaceutical composition as claimed in claim 1, wherein said ointment base comprises: one or more waxy materials, one or more co-solvents, one or more acids, one or more thickeners, one or more preservatives, one or more chelating agents, one or more humectants, and water, wherein the one or more waxy materials comprise at least one of Polyethylene Glycol (PEG) 400, PEG 500, PEG 1000, PEG 1200, PEG 1500, PEG 1800, PEG 2000, PEG 2200, PEG 3550, or PEG 4000, and wherein the one or more waxy materials are present in an amount between 5% (w/w) to 80% (w/w), wherein the one or more co-solvents comprise at least one of: Propylene Glycol, Hexylene Glycol, PEG 200, PEG 300, PEG 400, or PEG 500, and wherein the one co-solvents are present in an amount between 5% (w/w) to 80% (w/w), wherein the one or more acids comprises at least one of: HCl, $H_2SO_4$, $HNO_3$, or Lactic acid, and wherein the one or more acids are present in an amount between 0.005% (w/w) to 1% (w/w), wherein the one of more thickeners comprises at least one of: Acrylamide/Sodium AcryloyldimethylTaurate Copolymer/Isohexadecane & Polysorbate 80, Microcrystalline Cellulose, Carboxymethyl Cellulose, Hydroxypropyl Methyl Cellulose, or Ethyl Cellulose and wherein the one or more thickeners are present in an amount between 0.05% (w/w) to 10% (w/w), wherein the one or more preservatives comprise at least one of: Methylparaben, Propylparaben, Chlorocresol, or Potassium sorbate, and wherein the one or more preservatives are present in an amount between 0.05% (w/w) to 2.0% (w/w), wherein the one or more chelating agents comprise Disodium EDTA, and wherein the one or more chelating agents are present in an amount between 0.05% (w/w) to 1% (w/w).

3. The pharmaceutical composition as claimed in any one of claim 1 or 2, wherein said chitosan has a degree of deacetylation of no less than 70%.

4. The pharmaceutical composition as claimed in any one of claim 1 or 2, wherein said chitosan has a bacterial endotoxin level of 100 IU/g.

5. The pharmaceutical composition as claimed in any one of claim 1 or 2, wherein said chitosan has a molecular weight in the range between 250,000 Da to 600,000 Da.

6. The pharmaceutical composition as claimed in claim 1, wherein said topical antibiotic pharmaceutically active agent is Mupirocin present in an amount of 2% (w/w).

7. The pharmaceutical composition as claimed in claim 1, wherein said biopolymer is Chitosan present in an amount of 0.05% (w/w).

8. The pharmaceutical composition as claimed in claim 1, wherein said hydrolyzed collagen of type I is present in an amount of 0.05% (w/w).

9. The pharmaceutical composition as claimed in claim 3, wherein said chitosan has a degree of deacetylation of no less than 80%.

10. The pharmaceutical composition as claimed in claim 1, wherein said ointment base comprises one or more waxy materials, one or more co-solvents, one or more acids, one or more thickeners, one or more preservatives, one or more chelating agents, one or more humectants, and water.

11. The pharmaceutical composition as claimed in claim 10,
wherein the one or more waxy materials are present in an amount between 5% (w/w) to 80% (w/w);
wherein the one or more co-solvents are present in an amount between 5% (w/w) to 80% (w/w);
wherein the one or more acids are present in an amount between 0.005% (w/w) to 1% (w/w);
wherein the one or more thickeners are present in an amount between 0.05% (w/w) to 10% (w/w);
wherein the one or more preservatives are present in an amount between 0.05% (w/w) to 2.0% (w/w); and
wherein the one or more chelating agents are present in an amount no greater than 1% (w/w).

12. The pharmaceutical composition as claimed in claim 11,
wherein each of the one or more waxy materials is selected from the group consisting of: PEG 400, PEG 500, PEG 1000, PEG 1200, PEG 1500, PEG 1800, PEG 2000, PEG 2200, PEG 3550, PEG 4000, and combinations thereof;
wherein each of the one or more co-solvents is selected from the group consisting of: Propylene Glycol, Hexylene Glycol, PEG 200, PEG 300, PEG 400, PEG 500, and combinations thereof;
wherein each of the one or more acids is selected from the group consisting of: HCl, $H_2SO_4$, $HNO_3$, Lactic acid, and combinations thereof;
wherein each of the one or more thickeners is selected from the group consisting of: Acrylamide/Sodium AcryloyldimethylTaurate Copolymer/Isohexadecane & Polysorbate 80, Microcrystalline Cellulose, Carboxymethyl Cellulose, Hydroxypropyl Methyl Cellulose, Ethyl Cellulose, and combinations thereof;
wherein each of the one or more preservatives is selected from the group consisting of: Methylparaben, Propylparaben, Chlorocresol, Potassium sorbate, and combinations thereof; and
wherein each of the one or more chelating agents is Disodium EDTA.

13. The pharmaceutical composition as claimed in claim 1, wherein the Mupirocin has a molecular weight of about 500.6 grams per mol (g/mol).

14. The pharmaceutical composition as claimed in claim 3, wherein said chitosan has a bacterial endotoxin level of 100 IU/g.

15. The pharmaceutical composition as claimed in claim 3, wherein said chitosan has a molecular weight in the range between 250,000 Da to 600,000 Da.

16. The pharmaceutical composition as claimed in claim 4, wherein said chitosan has a molecular weight in the range between 250,000 Da to 600,000 Da.

17. The pharmaceutical composition as claimed in claim 1, wherein said pharmaceutical composition has a water content of no greater than 2% (w/w).

18. The pharmaceutical composition as claimed in claim 1, wherein the ointment base is a non-aqueous ointment base.

19. The pharmaceutical composition as claimed in claim 1, wherein said hydrolyzed collagen of type I is present in an amount of 0.5% (w/w).

* * * * *